United States Patent
Michalopoulos

(10) Patent No.: US 11,219,637 B1
(45) Date of Patent: Jan. 11, 2022

(54) INHALATION DELIVERY METHODS AND COMPOSITIONS FOR VITAMIN B12

(71) Applicant: George Michalopoulos, Los Angeles, CA (US)

(72) Inventor: George Michalopoulos, Los Angeles, CA (US)

( * ) Notice: Subject to any disclaimer, the term of this patent is extended or adjusted under 35 U.S.C. 154(b) by 0 days.

(21) Appl. No.: 16/733,145

(22) Filed: Jan. 2, 2020

Related U.S. Application Data

(63) Continuation of application No. 16/109,294, filed on Aug. 22, 2018, now abandoned, which is a continuation of application No. 16/045,676, filed on Jul. 25, 2018, now abandoned.

(60) Provisional application No. 62/536,780, filed on Jul. 25, 2017.

(51) Int. Cl.
| | | |
|---|---|---|
| *A61K 31/714* | (2006.01) | |
| *A61K 9/00* | (2006.01) | |
| *A61K 47/10* | (2017.01) | |

(52) U.S. Cl.
CPC .......... *A61K 31/714* (2013.01); *A61K 9/0078* (2013.01); *A61K 47/10* (2013.01)

(58) Field of Classification Search
CPC ..... A61K 31/714; A61K 9/0078; A61K 47/10
See application file for complete search history.

(56) References Cited

U.S. PATENT DOCUMENTS

| | | |
|---|---|---|
| 2013/0131007 A1 | 5/2013 | Brown |
| 2020/0108009 A1* | 4/2020 | Danek .................. A61K 31/465 |

OTHER PUBLICATIONS

CDC (https://www.fda.gov/tobacco-products/products-ingredients-components/vaporizers-e-cigarettes-and-other-electronic-nicotine-delivery-systems-ends, downloaded on Nov. 3, 2020).*
Umezawa (Particle and Fibre Toxicology; 2013, 10:64, pp. 1-10).*
Forum (https://forums.phoenixrising.me/threads/methylcobalamin-inhalation-therapy.33045/ (Posted Oct. 8, 2014).*
Juzeniene (Journal of Photochemistry and Photobiology B: Biology 122, 2013, 7-14).*
Shiran (The Israel Medicine Association Journal, 17 (5) 2015, 288-92).*
Smith (Transactions of the American Clinical and Climatological Association; 1953; 64; 27-39).

* cited by examiner

*Primary Examiner* — Pancham Bakshi
(74) *Attorney, Agent, or Firm* — Fresh IP PLC; Clifford D. Hyra; Aubrey Y Chen

(57) ABSTRACT

A method for effective delivery of vitamin B12 to a human being involves positioning a delivery device containing a mixture comprising a form of vitamin B12 and water such that, when activated, the delivery device places at least a portion of the mixture inside of a users mouth in a form suitable for inhalation, and activating the delivery device while or before the user inhales. The form of vitamin B12 may be cyanocobalamin, methylcobalamin, hydroxocobalamin, and/or adenosylcobalamin. The delivery device may be an aerosolizer, atomizer, vaporizer, or humidifier. The mixture may also include flavorings. Water may be 20% or less of the mixture by volume. The mixture may contain no nicotine, propylene glycol, or diacetyl. A method for vitamin B12 supplementation includes determining that a person has a disorder causing the person to have a reduced ability to process B-vitamins and administering methylcobalamin by inhalation.

11 Claims, 3 Drawing Sheets

100 → Mix liquid ingredients — 102

Load mixture — 104

Position aerosolizer — 106

Activate aerosolizer — 108

FIG. 1

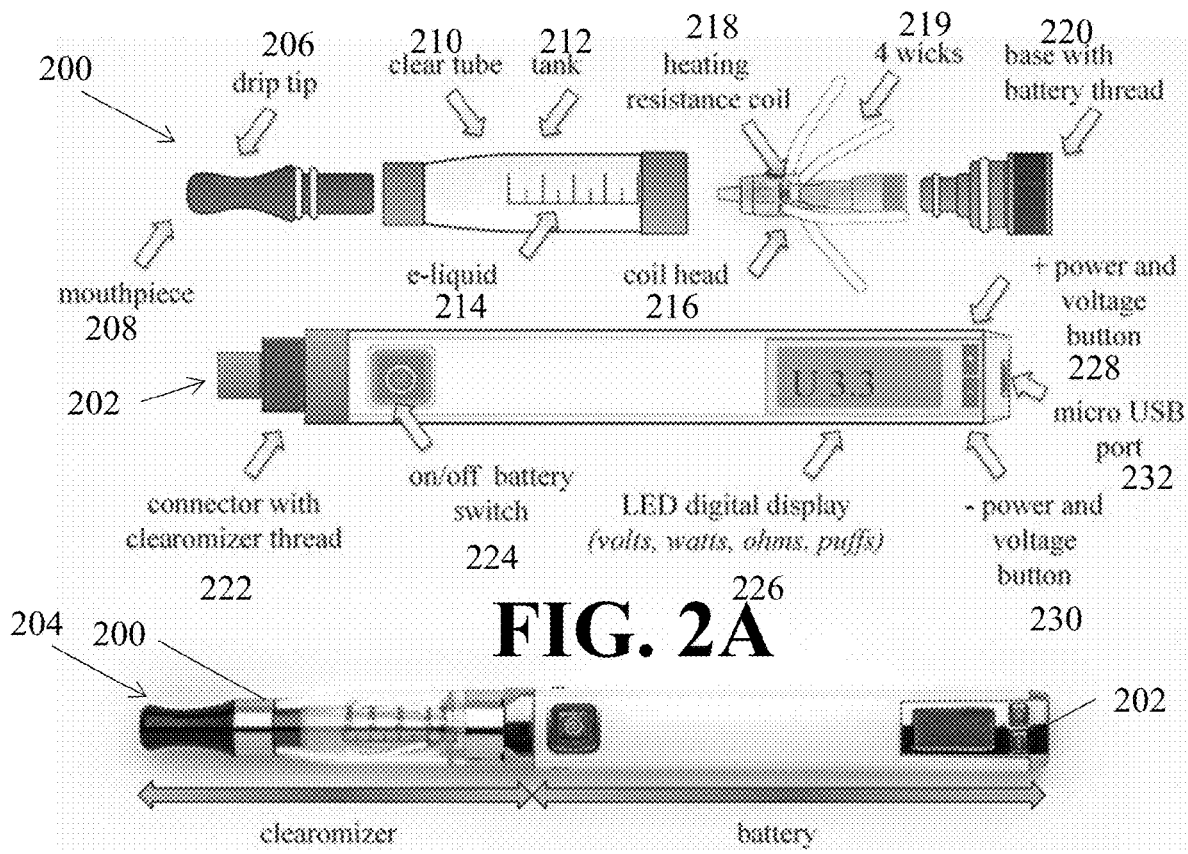
FIG. 2A
FIG. 2B
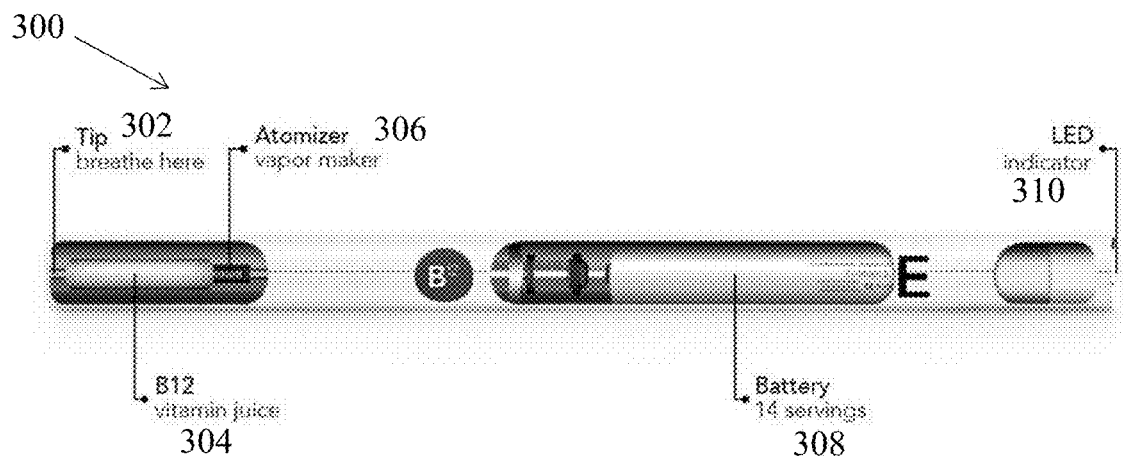
FIG. 3

INHALATION DELIVERY METHODS AND COMPOSITIONS FOR VITAMIN B12

This application is a continuation of U.S. application Ser. No. 16/109,294, filed Aug. 22, 2018, which is a continuation of U.S. application Ser. No. 16/045,676 filed Jul. 25, 2018, which claims the benefit of U.S. Provisional Application No. 62/536,780, filed Jul. 25, 2017, which are hereby incorporated by reference in their entirety.

FIELD OF THE DISCLOSURE

The present application relates generally to the field of vitamin supplementation.

BACKGROUND

Vitamin B12 supplementation is recognized to be beneficial for many people. Cyanocobalamin is a synthetic form of vitamin B12 that has been used for supplementation. With oral supplements, it is often difficult to achieve a dose as high as desired. Some people take B12 injections to achieve the dose they desire; however, injections are inherently inconvenient and pose health concerns. Some people also do not readily absorb vitamin B12 from supplements, and therefore find it difficult to achieve a desired absorption through traditional methods.

Needs exist for improved systems, methods and compositions for vitamin B12 supplementation.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description. Rather, the scope of the invention is defined by the appended claims.

In certain embodiments, the disclosed embodiments may include one or more of the features described herein.

A new method for effective delivery of vitamin B12 to a human being involves placing a delivery device containing a mixture comprising a form of vitamin B12 and water in a position such that, when activated, the delivery device places at least a portion of the mixture inside of a user's mouth in a form suitable for inhalation and activating the delivery device while the delivery device is in the position and while or before the user inhales. In some embodiments, the delivery device is activated and after the activation, the user does not exhale or remove the delivery device from the position before inhaling. The delivery device may be activated within one second prior to the user inhaling. The form of vitamin B12 in some embodiments includes cyanocobalamin, methylcobalamin, hydroxocobalamin, and/or adenosylcobalamin. In some embodiments the form of vitamin B12 includes methylcobalamin, hydroxocobalamin, and/or adenosylcobalamin. The mixture may also include vegetable glycerin or propylene glycol. The delivery device may be an aerosolizer. In some embodiments activating the delivery device sprays at least a portion of the mixture into the user's mouth. The method may also include inhaling. The method may also include activating the delivery device while the user inhales. The delivery device may be an atomizer, vaporizer, or humidifier. The method may also include loading the mixture into the aerosolizer. The method may also include mixing together a) methylcobalamin, hydroxocobalamin, and/or adenosylcobalamin, b) vegetable glycerin or propylene glycol, and c) water to form the mixture. The mixture may also include flavorings. In some embodiments, water does not exceed 20% of the mixture by volume. In some embodiments, the mixture contains no nicotine, propylene glycol, or diacetyl. In some embodiments, the form of vitamin B12 includes methylcobalamin.

A new composition for effective delivery of vitamin B12 to a human being by inhalation includes methylcobalamin, hydroxocobalamin, and/or adenosylcobalamin, vegetable glycerin or propylene glycol, and water. The composition may also include one or more flavorings. In some embodiments, water does not exceed 20% of the composition by volume. In some embodiments, the composition contains no nicotine, propylene glycol, or diacetyl. The composition in some embodiments includes methylcobalamin. At least for ultrasonic vapor applications, the composition may include only water and vitamin B12, the vitamin B12 being present in the solution in a concentration of, for example, >1000 mcg/ml.

A new method for vitamin B12 supplementation involves determining that a person has a disorder causing the person to have a reduced ability to process one or more forms of B-vitamins and convert them into a usable form in the body and administering methylcobalamin to the person in aerosol form or in water vapor, for inhalation. In some embodiments, the person is determined to have a MTHFR gene mutation. In some embodiments, the methylcobalamin is administered as part of a mixture also comprising vegetable glycerin and water. In some embodiments, the determined disorder includes anemia, pernicious anemia, and/or advanced age. In some embodiments, administering methylcobalamin involves administering at least 500 mcg of methylcobalamin in one day or in one week. For example, 500 mcg of methylcobalamin may be administered in a single daily or weekly dose. Depending on the concentration of the methylcobalamin in the solution used to administer the methylcobalamin, 500 mcg of methylcobalamin may be administered in 0.01 mL or more of solution. The concentration of methylcobalamin in solution for a vaporizer/electronic cigarette application in some embodiments is 1,000 mcg/mL or higher, in preferred embodiments 2,000 mcg/mL or higher. Such concentrations have been surprisingly found to have a beneficial effect on absorption, substantially increasing levels of B12 in a user's blood immediately after treatment (within about 5 minutes) and persistently, where lower concentrations result in no effect on the user's blood levels of B12. In other applications (e.g. humidifier), the concentration may be adjusted so that the constitution of the gas reaching the user is equivalent to that achieved using the above concentrations in vaporizer applications.

These and further and other objects and features of the invention are apparent in the disclosure, which includes the above and ongoing written specification, with the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein:

FIG. 1 illustrates a method of aerosol delivery for methylcobalamin, hydroxocobalamin, and adenosylcobalamin, according to an embodiment of the present invention.

FIGS. 2A-B illustrates an electronic cigarette exploded (2A) and assembled (2B).

FIG. 3 illustrates another electronic cigarette.

DETAILED DESCRIPTION

Figure 4:
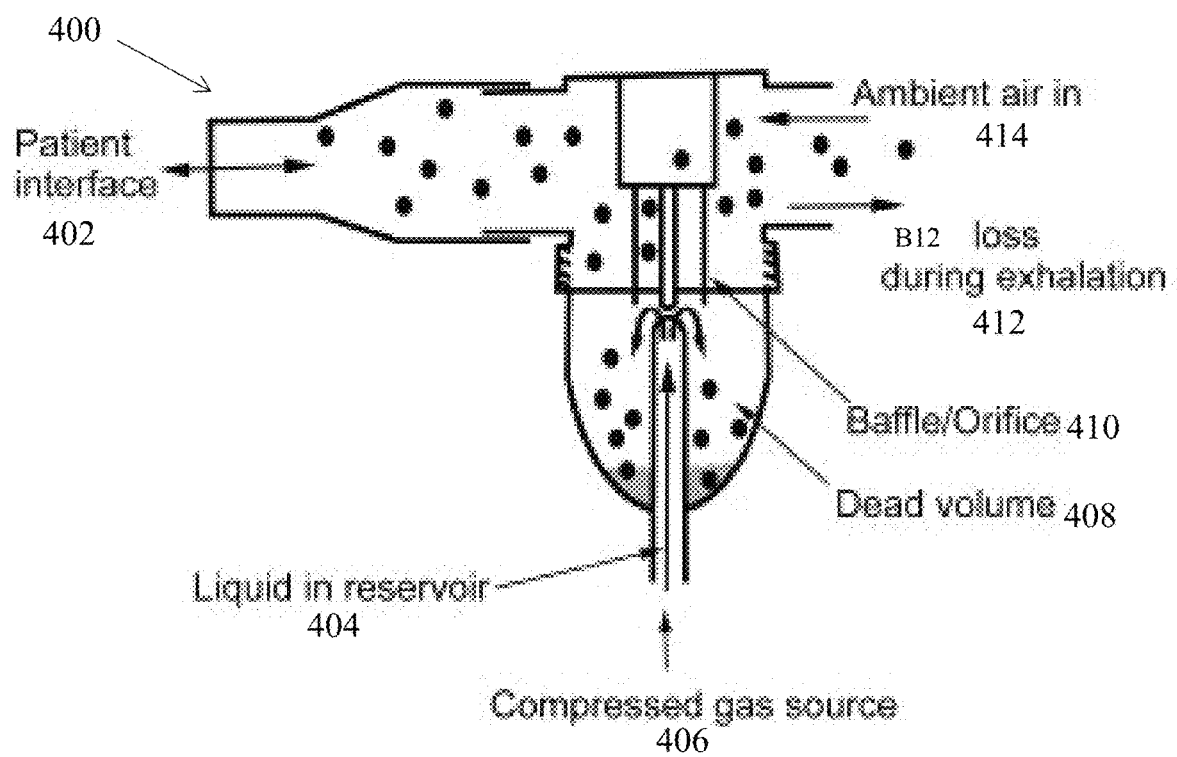
FIG. 4 illustrates a nebulizer.

Inhalation delivery methods and compositions for vitamin B12 will now be disclosed in terms of various exemplary embodiments. This specification discloses one or more embodiments that incorporate features of the invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted.

The description is not to be taken in a limiting sense, but is made merely for the purpose of illustrating the general principles of the invention, since the scope of the invention is best defined by the appended claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an" and "the" are intended to include the plural forms as well, unless the context clearly indicates otherwise.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

FIG. 1 illustrates a new method 100 for effective delivery of vitamin B12 to a human being, according to an embodiment of the present invention. In this embodiment, methylcobalamin, vegetable glycerin or propylene glycol, and water are mixed 102 to form a mixture. Water does not exceed 20% by volume of the mixture.

The mixture is loaded 104 into an aerosolizer. The aerosolizer may be, for example, an electronic cigarette, also called an e-cigarette. Exemplary e-cigarettes are shown in FIGS. 2 and 3. The loading may be accomplished by loading the mixture into a cartridge for the e-cigarette (or other aerosolizer) and then loading the cartridge into the aerosolizer. In other embodiments, the cartridge or a disposable aerosolizer may be pre-loaded with the mixture. For a disposable aerosolizer particularly, the aerosolizer may come with the mixture pre-loaded from the factory, and a loading step may not be required of the user.

The aerosolizer containing the mixture is positioned 106 such that, when activated, the aerosolizer sprays its contents into a user's mouth. The aerosolizer is activated 108 while the user inhales, spraying the mixture into the user's mouth where the mixture is drawn into the user's lungs, where it is absorbed into the user's bloodstream.

FIGS. 2A-B illustrate a microprocessor-controlled, variable-voltage/wattage, personal electronic-cigarette 204 with LED digital display 226 (volts or watts, puff count, ohmic resistance), equipped with a transparent clearomizer 200 and changeable dual-coil head 216. It offers a wide range of settings (power, voltage adjustments) and the option of using different resistance coils. FIG. 2A shows the electronic-cigarette 204 in exploded (disassembled) form for clarity, while FIG. 2B shows the electronic-cigarette 204 fully assembled. Mouthpiece 208 has drip tip 206 and fits into clear tube 210 of tank 212 which contains the e-liquid 214. For insertion into the tank 212 there is coil head 216 with heating resistance coil 218 and four wicks 219 which extend into the e-liquid 214, and base 220 with battery thread for connecting to the battery portion 202 of the electronic-cigarette 204.

Battery portion 202 includes connector 222 for mating with the threats of the clearomizer portion 200, on/off battery switch 224, LED digital display 226, +/1 power and voltage buttons 228, 230, and micro USB port 232.

FIGS. 2A-B are distributed under the terms and conditions of the Creative Commons Attribution license (http://creativecommons.org/Aicenses/by/4.0/) and are authored by Christian Giroud, Mariangela de Cesare, Aurelie Berthet, Vincent Varlet, Nicolas Concha-Lozano, and Bernard Favrat, and is available at http-/www.ncbi.nlm.nih.gov/pmc/articles/PMC4555324/.

FIG. 3 illustrates another electronic cigarette 300, having tip 302 from which a user inhales, B12 vitamin juice 304, atomizer 306 for converting the B12 vitamin juice into vapor, battery 308 for powering the atomizer 306, and LED indicator 310 for displaying battery power.

A new composition for effective aerosol delivery of vitamin B12 to a human being includes methylcobalamin, hydroxocobalamin, and/or adenosylcobalamin, vegetable glycerin or propylene glycol, and water. In some embodiments, the composition may also include one or more flavorings. In some embodiments, water does not exceed 20% of the composition by volume. In a preferred embodiment, the composition comprises methylcobalamin, has no more than 20% water by volume, and contains no nicotine, propylene glycol, or diacetyl.

Figure 5:
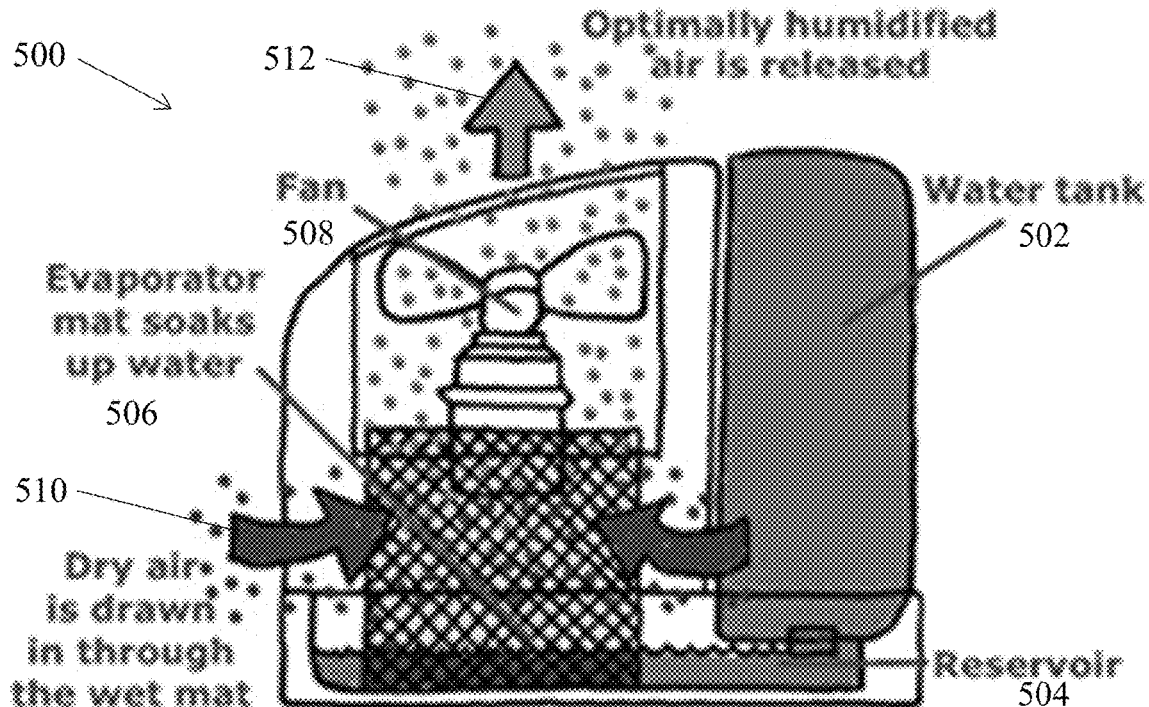
FIG. 5 illustrates a humidifier.

FIGS. 4 and 5 illustrate alternative, non-aerosolizer delivery devices for vitamin B12. FIG. 4 illustrates a nebulizer 400 and FIG. 5 illustrates a humidifier 500. In either, a mixture of vitamin B12 and water is used as the liquid in the reservoir. In some embodiments, other ingredients may also be included in the mixture. As in other embodiments, the form of vitamin B12 used may be cyanocobalamin, methylcobalamin, hydroxocobalamin, and/or adenosylcobalamin, and in a preferred embodiment methylcobalamin. In such embodiments, water may be, and typically is, more than 20% of the mixture. The delivery device is used as normal to deliver the B12 to a user by inhalation. The user may mix the ingredients to make the mixture and load the mixture into the reservoir of the delivery device.

Nebulizer 400 has a patient interface 402 where a patient places their mouth to inhale the liquid 404 in the reservoir. When a patient inhales through patient interface 402, ambient air 414 is drawn into the nebulizer 400 Compressed gas source 406 interacts with baffle/orifice 410 and aerosolizes the liquid 404 in the reservoir so that it is inhaled by the patient along with the ambient air 414. Some B12 412 is lost out the same channel through which ambient air 414 is drawn in when the patient exhales.

Humidifier 500 has a water tank 502 (which also includes B12 and optionally other ingredients as noted above) which fills reservoir 504, into which an evaporator mat 506 is inserted and where it soaks up the water (and B12 and/or other ingredients). Fan 508 draws dry air 510 from outside the humidifier 500 through the evaporator mat 506 soaked with water/B12, which causes the dry air to become humidified with the B12-carrying water. This humidified air 512 is expelled out the top of the humidifier by the fan 508 and into the air around the humidifier 500, where a user inhales it.

Many people report feeling energized by B12 supplementation. The disclosed compositions can be used without any caffeine, sugar, calories or nicotine.

It has been discovered that B12 can be hundreds or thousands of times more effectively absorbed by inhalation than by ingestion in pill form. Administering B12 as aerosol as described allows a user to carry, in an exemplary aerosolizer, hundreds of doses in a single aerosolizer, 14,000 mcg total or about fourteen times as much B12 as is typically administered in a B12 injection. A B12 aerosolizer carries a modest cost and is simple and inconspicuous to use, in comparison to B12 injections which are painful and inconvenient and can cost hundreds of dollars.

It has surprisingly been discovered that methylcobalamin administered in inhalable form as disclosed is more bioavailable than other forms of B12. It has further been surprisingly discovered that methylcobalamin administered in inhalable form as disclosed is more easily absorbed than other forms of B12 by those having a methylenetetrahydrofolate reductase (MTHFR) genetic mutation, which causes bearers to have a greatly reduced ability to process B-vitamin supplements and convert them into a usable form in the body. When a person is determined to have MTHFR or another condition that causes the person to have a reduced ability to process B-vitamin supplements and convert them into a usable form in the body, the person may be administered methylcobalamin by inhalation for proper B12 supplementation.

The invention is not limited to the particular embodiments illustrated in the drawings and described above in detail. Those skilled in the art will recognize that other arrangements could be devised. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application. While the invention has been described with reference to specific illustrative embodiments, modifications and variations of the invention may be constructed without departing from the spirit and scope of the invention as set forth in the following claims.

I claim:

1. A method for treating a vitamin B12 disorder, comprising:
    identifying a vitamin B12 disorder in a patient, wherein the disorder comprises a deficiency in B-vitamins; and
    administering a liquid mixture consisting of methylcobalamin and water to the patient by inhalation, thereby treating the vitamin B12 disorder.

2. The method of claim 1, wherein the patient has a MTHFR gene mutation.

3. The method of claim 1, wherein the disorder is anemia, pernicious anemia, and/or advanced age.

4. The method of claim 1, wherein the administering a liquid mixture consisting of methylcobalamin and water to the patient by inhalation administers at least 500 micrograms of methylcobalamin in one day or in one week.

5. The method of claim 1, wherein the inhalation is performed by the patient.

6. The method of claim 1, wherein the inhalation is performed through a vaporizer and/or a humidifier.

7. The method of claim 6, wherein the inhalation is performed through a battery-powered vaporizer.

8. The method of claim 6, wherein administering the liquid mixture by inhalation further comprises:
    placing the liquid mixture consisting of methylcobalamin and water into the vaporizer; and
    utilizing the vaporizer to convert at least part of the liquid mixture into an inhalation mixture.

9. The method of claim 8, wherein the vaporizer comprises one or more heating elements that convert the at least part of the liquid mixture into the inhalation mixture.

10. The method of claim 8, wherein the vaporizer is an electronic cigarette, wherein the placing step further comprises placing the liquid mixture into an electronic cigarette cartridge and placing the electronic cigarette cartridge into the electronic cigarette.

11. The method of claim 6, wherein the administering the liquid mixture by inhalation step further comprises:
    filling a water tank of the humidifier with the liquid mixture;
    inserting an evaporation mat into the humidifier; and
    operating the humidifier such that the evaporation mat soaks up the liquid mixture, thereby resulting in air passing through the humidifier becoming humidified with the liquid mixture.

* * * * *